United States Patent
Becker et al.

(10) Patent No.: US 10,332,626 B2
(45) Date of Patent: Jun. 25, 2019

(54) SYSTEM AND METHOD FOR DATA PROCESSING

(71) Applicant: Agfa HealthCare GmbH, Bonn (DE)

(72) Inventors: Hendrik Becker, Mortsel (BE); Ullrich Rentel, Mortsel (BE)

(73) Assignee: AGFA HEALTHCARE GMBH, Bonn (DE)

( * ) Notice: Subject to any disclaimer, the term of this patent is extended or adjusted under 35 U.S.C. 154(b) by 296 days.

(21) Appl. No.: 14/903,853

(22) PCT Filed: Jul. 8, 2014

(86) PCT No.: PCT/EP2014/064587
§ 371 (c)(1),
(2) Date: Jan. 8, 2016

(87) PCT Pub. No.: WO2015/007570
PCT Pub. Date: Jan. 22, 2015

(65) Prior Publication Data
US 2016/0154938 A1    Jun. 2, 2016

(30) Foreign Application Priority Data
Jul. 15, 2013   (EP) .................................... 13176501

(51) Int. Cl.
*G16H 10/60* (2018.01)
*G16H 40/20* (2018.01)

(52) U.S. Cl.
CPC ............ *G16H 40/20* (2018.01); *G16H 10/60* (2018.01)

(58) Field of Classification Search
None
See application file for complete search history.

(56) References Cited

U.S. PATENT DOCUMENTS

| 6,381,576 | B1 |  | 4/2002 | Gilbert |
| 7,483,058 | B1 | * | 1/2009 | Frank ..................... H04N 5/232 348/222.1 |
| 8,180,783 | B1 | * | 5/2012 | Fletcher ............ G06F 17/30684 707/723 |
| 9,832,379 | B1 | * | 11/2017 | Neglur ............... H04N 5/23241 |
| 2003/0225754 | A1 | * | 12/2003 | Chen ................. G06F 17/30286 |
| 2004/0267510 | A1 |  | 12/2004 | Becker |

(Continued)

FOREIGN PATENT DOCUMENTS

WO    2008/079341 A2    7/2008

OTHER PUBLICATIONS

Official Communication issued in International Patent Application No. PCT/EP2014/064587, dated Jan. 8, 2015.

*Primary Examiner* — Michael Lebentritt
(74) *Attorney, Agent, or Firm* — Keating and Bennett, LLP (57) ABSTRACT

A system and corresponding method for data processing, in particular sensor data processing, includes at least two first modules that generate or capture first data, at least one second module that retrieves the first data from first modules which correspond to first modules of at least one predefined set of first modules, and a third module that processes the first data which were retrieved by the at least one second module. The relevant data captured by a plurality of different data capturing modules, in particular sensors, are made available in a processing module in a fast and reliable manner.

14 Claims, 6 Drawing Sheets

(56) References Cited

U.S. PATENT DOCUMENTS

| | | | |
|---|---|---|---|
| 2005/0288893 A1* | 12/2005 | Gassner | H01L 21/67253 |
| | | | 702/182 |
| 2011/0201900 A1 | 8/2011 | Zhang et al. | |
| 2012/0197596 A1* | 8/2012 | Comi | G06F 9/5066 |
| | | | 702/188 |
| 2013/0041962 A1* | 2/2013 | Wang | H04L 51/12 |
| | | | 709/206 |
| 2014/0304429 A1* | 10/2014 | Softky | G06F 3/04842 |
| | | | 710/8 |
| 2015/0106623 A1* | 4/2015 | Holman | H04L 63/0457 |
| | | | 713/171 |
| 2015/0106628 A1* | 4/2015 | Holman | G06F 21/602 |
| | | | 713/189 |
| 2015/0106947 A1* | 4/2015 | Holman | G06F 21/62 |
| | | | 726/26 |
| 2015/0248392 A1* | 9/2015 | Watanabe | G06F 17/243 |
| | | | 715/226 |
| 2016/0117448 A1* | 4/2016 | Van De Craen | G06F 21/6245 |
| | | | 705/3 |
| 2016/0267921 A1* | 9/2016 | Dang | G06T 11/60 |
| 2016/0287470 A1* | 10/2016 | Lewis | A61H 31/005 |

\* cited by examiner

SYSTEM AND METHOD FOR DATA PROCESSING

CROSS-REFERENCE TO RELATED APPLICATIONS

This application is a 371 National Stage Application of PCT/EP2014/064587, filed Jul. 8, 2014. This application claims the benefit of European Application No. 13176501.8, filed Jul. 15, 2013, which is incorporated by reference herein in its entirety.

BACKGROUND OF THE INVENTION

1. Field of the Invention

The invention relates to a system and a method for data processing, in particular for sensor data processing, as defined below.

2. Description of the Related Art

In prior art data processing systems, data captured by a plurality of different data capturing modules, e.g. optical, acoustic or temperature sensors, are forwarded to a central processing module, e.g. a sensor data evaluation module, in which the forwarded data are processed. Usually, captured sensor data are forwarded to the sensor data evaluation module by each sensor automatically, for example upon generation of sensor data dependent from electromagnetic or acoustic waves emerging from an object under investigation and received by the sensor. By this, however, it cannot always be ensured that all relevant sensor data captured or generated by several different kinds of sensors are forwarded and processed in the sensor data evaluation module.

SUMMARY OF THE INVENTION

Preferred embodiments of the invention provide a system and a method for data processing, in particular sensor data processing, which ensures that relevant data captured by a plurality of different data capturing modules are made available in the processing module in a fast and reliable manner.

The preferred embodiments are achieved by the system and method defined below.

The system for data processing according to a preferred embodiment of the invention comprises at least two first modules, each of said first modules being adapted for generating or capturing first data, at least one second module, adapted for retrieving first data from those first modules which correspond to first modules of at least one pre-defined set of first modules, and a third module, adapted for processing the first data which were retrieved by the at least one second module.

In the method for data processing according to a preferred embodiment of the invention at least two first modules generate or capture first data, at least one second module retrieves first data from those first modules which correspond to first modules of at least one pre-defined set of first modules, and a third module processes the first data which were retrieved by the at least one second module.

Preferred embodiments of the invention are based on the approach to provide a second module, which is configurable and/or customizable to the effect that at least one set of first modules can be pre-defined, preferably by a user. Moreover, the second module is adapted for calling only those first modules corresponding to the at least one pre-defined set of first modules, for receiving first data from the called first modules and for forwarding the received data to the third module in which the received data are processed. As a result, all first data captured by a desired, i.e. pre-defined, set of first modules are available for processing in the third module, irrespective of the different moments in time in which the first data have been generated or captured by respective first modules of the pre-defined set of first modules.

In summary, preferred embodiments of the invention ensure that all desired and/or relevant data captured by different data capturing modules are present in the processing module. Within the meaning of the present invention the term "module" preferably relates to an electronic device and/or a software entity which is configured to execute specified functions.

For example, the term "first module" preferably relates to a device and/or an electronic circuit and/or a software entity which is configured to generate and/or capture data. E.g., the first module can be or can comprise a medical device, a sensor or an input unit, like a barcode scanner and/or a keyboard, enabling data input.

The term "second module" preferably relates to a device and/or an electronic circuit and/or a software entity which is configured to retrieve data and/or obtain data and/or forward data. Further, the second module is preferably configurable by a user such that the second module retrieves and/or obtains and/or forwards only data of a pre-defined data set, which has been pre-defined by a user.

Preferably, the term "third module" relates to a device and/or an electronic circuit and/or a software entity which is configured to process data, e.g. by calculating values based on retrieved or obtained data (e.g. by summation, multiplication, division etc.) and/or compiling retrieved or obtained data and/or generating a document based on retrieved or obtained data or on calculated values based on retrieved or obtained data.

Within the meaning of the present invention, the term "pre-defined set of first modules" preferably relates to two or more first modules constituting a set of first modules, wherein the two or more first modules of the set of first modules are pre-definable by an according user input into the second module.

Preferably, the second module is configured to call only those first modules that constitute the at least one pre-defined set of first modules and/or to receive or obtain first data from the called first modules and/or to forward the received or obtained data to the third module in which the received or obtained data are processed.

According to a preferred embodiment of the invention, the at least one second module being adapted for forwarding the retrieved first data to the third module such that the retrieved first data are available in the third module at a certain, in particular pre-defined, point of time. Preferably, said certain or pre-defined point of time corresponds to the point of time at which the processing of the retrieved first data commences. By this, it is ensured that all of the desired first data can be considered in the subsequent processing step. This is of particular advantage in cases where the third module is adapted for calculating at least one second data from at least two of the retrieved first data. Because it is ensured that all of the desired first data are available at the beginning of the calculation procedure, the second data calculated from the retrieved first data, e.g. by summation, subtraction, multiplication or division, corresponds to the correct value.

It is also preferred that the third module is adapted for requesting the second module to forward the retrieved first data to the third module. Preferably, the third module sends a request to the second module shortly before a processing of the retrieved first data shall start and/or upon a user request to the third module to start with a processing of first data.

Further it is particularly preferred that, first, the third module sends a request to the second module to forward first data to the third module, second, upon receipt of the request from the third module the second module sends a request to the pre-specified first modules to forward first data captured by the pre-specified first modules to the second module and, third, the second module forwards the first data retrieved from the pre-specified first modules to the third module.

The aforementioned embodiments—alone or in combination—further contribute to ensure that all of the desired first data of the pre-specified first modules are available at the third module in order to be altogether and/or commonly processed. By this, e.g. all sensor data captured by one or more pre-specified optical sensors and acoustic sensors can be considered in the processing step at the same time.

According to another preferred embodiment of the invention, the at least one second module being adapted for selecting at least one pre-defined set of first modules from multiple pre-defined sets of first modules and for retrieving first data from those first modules which correspond to first modules of the at least one selected pre-defined set of first modules. The multiple pre-defined sets of first modules can be established or defined, e.g. by a user when applying the system or method in continuous or daily use or when setting up the system or method for the first time, e.g. in the manufacturing process. By establishing or defining multiple pre-defined sets of first modules, from which at least one set of first modules can be chosen, the system and method according to preferred embodiments of the invention can be easily adapted to various applications in which first data from different first modules are to be processed in the third module.

Basically, the system and method can be configured such that the at least one pre-defined set of first modules can be manually, e.g. by a user, selected from multiple pre-defined sets of first modules.

Alternatively or additionally, it is preferred that the third module is adapted for processing the retrieved first data dependent upon a given processing mode and that the at least one second module being adapted for automatically selecting at least one pre-defined set of first modules from multiple pre-defined sets of first modules dependent upon the given processing mode. Preferably, to each processing mode of the third module, i.e. to each kind of processing of first data, a respective set of first modules, from which captured first data are retrieved by the second module and forwarded to the third module, is assigned. In this manner, it is ensured that all necessary first data, which are required with a certain processing mode, are available at the third module, in particular at a pre-defined point in time.

Within the meaning of the present invention, the term "processing mode" preferably relates to a pre-defined kind of processing of the first data, e.g. by calculating values based on retrieved or obtained data, like summation, and/or compiling retrieved or obtained data and/or generating a document based on retrieved or obtained data or calculated values based on retrieved or obtained data.

Preferably, the given processing mode depends upon a given object, to which the captured or generated first data relate. Additionally or alternatively, the third module is adapted for automatically selecting the processing mode dependent upon the given object, to which the captured or generated first data relate. For example, first data captured from a first object or from a first kind of objects are processed in a first processing mode, whereas first data captured from a second object or a second kind of objects are processed in a second processing mode etc. In this way, it is ensured that first data captured in relation to a given object or kind of objects are available for data processing according to a processing mode which is associated with the given object or kind of objects, respectively.

Within the meaning of the present invention, the term "given object" preferably relates to a patient and/or a medical case.

According to a further preferred embodiment, the at least one second module being adapted for assigning a processing mode to a pre-defined set of first modules. Thus, first data retrieved from each pre-defined set of first modules are processed according to the processing mode assigned thereto. For example, first data retrieved from a first pre-specified set of first modules are processed in a first processing mode, whereas first data retrieved from a second pre-specified set of first modules are processed in a second processing mode. By this, it is ensured that first data captured by a certain set of first modules are always processed according to a processing mode associated with that certain set of first modules.

It is also preferred that the at least one second module is adapted for generating and/or storing one or more pre-defined sets of first modules. Alternatively or additionally, the second module is adapted for receiving pre-defined sets of first modules, e.g. via an interface or a user input unit.

According to a further preferred embodiment of the invention, the third module is adapted for generating second data based on the processing of the first data. Further, the third module can be adapted for generating an output, in particular via a display and/or a hardcopy device, of the second data. For example, the second data are calculated from the first data by summation, subtraction, multiplication or division. Because of the second module's request to a pre-specified set of first modules to forward captured first data, it can be ensured that all necessary first data, i.e. all first data captured by the pre-specified set of first modules, are available for the calculation of the second data from the first data yielding complete and accurate calculation results.

Moreover, it is preferred that the at least two first modules are adapted for generating and/or capturing the first data upon one or more events related to an object. One or more events related to the object may be, e.g., a registration of the object or a start or termination of a treatment of the object. By this, it is ensured that first data are available as soon as a pre-defined event has occurred. In combination with retrieving first data generated and/or captured by a pre-defined set of first modules it can be ensured that in the third module all event-related first data of the pre-specified set of first modules are considered in the processing step. Accordingly, in the result of the processing of the first data, e.g. in a calculated sum of values corresponding to the first data, all relevant information about all of the events related to the object is considered.

Apart from processing sensor data, the invention and its preferred embodiments can be advantageously applied in other fields of data processing. Preferably, the first modules for generating or capturing first data can be any kind of data capturing modules, e.g. modules for capturing first data relating to treatments and/or services rendered to a patient or in connection with a medical case, e.g. in a hospital. Preferably, the second module can be a service collector module for retrieving first data from a pre-defined set of said first modules. Preferably, the third module can be a billing module for processing the first data which were retrieved by the service collector module and for generating a bill based on the retrieved first data and/or relating to the services captures by the first modules of the pre-defined set of said first modules. Accordingly, one or more events related to the object preferably correspond to a treatment of and/or a service rendered to the object, in particular a patient or a medical case. Moreover, the first data preferably relate to a treatment of and/or a service rendered to an object, in particular a patient or a medical case.

Further advantages, features and examples of the present invention will be apparent from the following description of following figures:

DETAILED DESCRIPTION OF THE PREFERRED EMBODIMENTS

Figure 1:
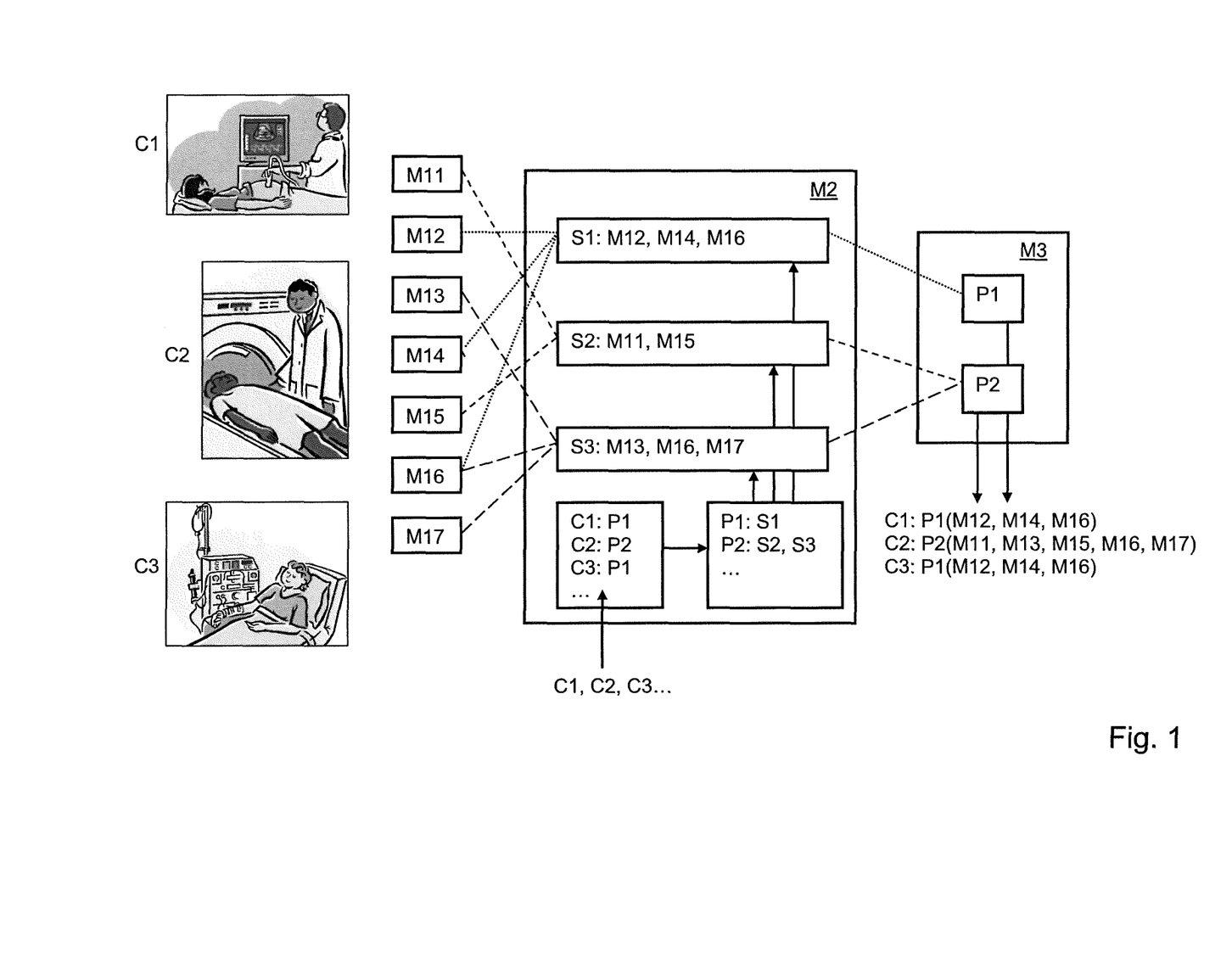
FIG. 1 shows an example of a first system for data processing.

FIG. 1 shows an example of a first system for data processing comprising first modules M11 to M17, a second module M2 and a third module M3. The first modules M11 to M17 are adapted for generating and/or receiving first data relating to objects C1, C2 and C3.

For example, the first modules M11 to M17 comprise and/or constitute medical devices and/or sensors, like optical sensors and/or ultrasound sensors for detecting electromagnetic radiation, e.g. x-rays or light, or ultrasound waves, respectively, emanating from objects C1, C2 and C3 under investigation, e.g. patients or body parts thereof. Based on the detected radiation or waves, respectively, first data are generated by the sensors.

Alternatively or additionally, at least a part of the first modules M11 to M17 are adapted to receive signals from sensors and/or medical devices, e.g. an x-ray, CT or MRT apparatus, an ultrasound apparatus or an electrocardiograph, relating to objects under investigation. Preferably, the received signals are converted by the first modules M11 to M17 into the first data. Alternatively, the received signals constitute the first data without prior conversion.

Preferably, the first modules M11 to M17 constitute and/or comprise input modules enabling an input of first data. For example, the first modules M11 to M17 comprise a barcode scanner for reading barcode data relating to services rendered to an object C1, C2 or C3, e.g. a patient, and/or a keyboard enabling a user, e.g. a nurse, to input first data relating to services rendered to the object C1, C2 or C3 into the first modules M11 to M17. The rendered services can be various kinds of activities in a hospital, like administering medicaments or medical consumables, performing a medical checkup or treatment, recruitment or discharge of patients.

The first data generated and/or received by the first modules M11 to M17 are forwarded to the second module M2, as indicated by dotted and dashed lines between the first modules M11 to M17 and the second module M2. Basically, the first modules M11 to M17 can be designed to forward first data, whenever first data have been generated or received by a first module. It is, however, particularly preferred that the second module M2 sends a request to one or more of the first modules M11 to M17 to forward possibly available first data to the second module M2. In other words, only those first modules M11 to M17 which get a respective request from the second module M2 will forward first data, if available, to the second module M2.

Preferably, the second module M2 sends according requests only to first modules of one or more pre-defined sets S1, S2 and S3 of first modules. In the example given in FIG. 1, in a first pre-defined set S1 three first modules M12, M14 and M16 are defined, whereas in a second pre-defined set S2 two first modules M11 and M15 and in a third pre-defined set S3 three first modules M13, M16 and M17 are defined.

When calling the first modules M12, M14 and M16 of the first pre-defined set S1 by the second module M2, first data available at the first modules M12, M14 and M16 at the point of time of the call are forwarded via the second module M2 to the third module M3 (see dotted lines), where the retrieved first data are processed dependent upon a first processing mode P1.

Accordingly, when calling the first modules of the second or third pre-defined set S2 or S3, only first data available at the first modules M11 and M15 or M13, M16 and M17, respectively, are forwarded via the second module M2 to the third module M3 (dashed lines), where the retrieved first data are processed dependent upon a second processing mode P2.

It is preferred that one or more pre-defined sets S1 to S3 of first modules can be defined, e.g. via user input into second module M2, by specifying respective first modules of one or more particular sets S1 to S3. By this, the second module M2 becomes configurable and/or customizable and can be easily adapted to desired applications, e.g. an evaluation of sensor data of various pre-defined sensors or a processing of data relating to various pre-defined medical devices or medical services.

Preferably, to a given object C1, C2 or C3 a particular processing mode P1, P2 for processing first data generated and/or received in connection with the object C1, C2 or C3 is assigned. In the present example of FIG. 1, in module M2 a lookup table is provided by which a certain processing mode P1 or P2 for a given object C1, C2 or C3 is retrieved or determined. For example, for a first and third object C1 and C3 a first processing mode P1 is retrieved ("C1: P1", "C3: P1"), whereas for a second object C2 a second processing mode P2 is retrieved ("C2: P2"). Preferably, the lookup table including the assignments between objects C1, C2, C3 and processing modes P1, P2 is freely configurable, e.g. via user input, or is generated automatically.

Moreover, it is preferred that to a certain processing mode P1, P2 one or more pre-defined sets S1, S2 and S3 of first modules are assigned. As obvious from the example given in FIG. 1, in module M2 a further lookup table is provided according to which the first pre-defined set S1 of first modules is assigned to the first processing mode P1 and the second and third pre-defined sets S2 and S3 of first modules are assigned to the second processing mode P2. The second module M2 is adapted for determining or retrieving one or more pre-defined sets S1 to S3 of first modules dependent upon the processing mode P1, P2 by the further lookup table.

According to the present example, for a desired object C1, e.g. a patient or a medical case, the second module M2 determines a first processing mode P1 assigned to this object C1. By the determined processing mode P1, the second module M2 subsequently determines the first pre-defined set S1 of first modules M12, M14 and M16 and sends a request to these modules to forward available first data, which were generated and/or received in first modules M12, M14 and M16 in connection with measurements on and/or treatments of object C1, to the second module M2 and/or the third module M3 (see dotted lines). In the third module M3 first data from first modules M12, M14 and M16 are processed according to processing mode P1. Same applies accordingly for a desired object C3.

For a desired object C2 a second processing mode P2 is retrieved. By the retrieved processing mode P2, the second module M2 determines the second and third pre-defined sets S2 and S3 of first modules M11, M15 and M13, M16, M17, respectively, and sends a request to these modules to forward available first data, which were generated and/or received these first modules in connection with measurements on and/or treatments of object C2, to the second module M2 and/or the third module M3 (see dashed lines). In the third module M3 first data from first modules M11, M13, M15, M16 and M17 are then processed according to processing mode P2.

By the first system described above it is ensured that all generated and/or captured first data required with a data processing step according to a given processing mode P1 and/or P2 are made available at the third module M3 at a certain point of time for being processed in the given processing mode P1 or P2.

Figure 2:
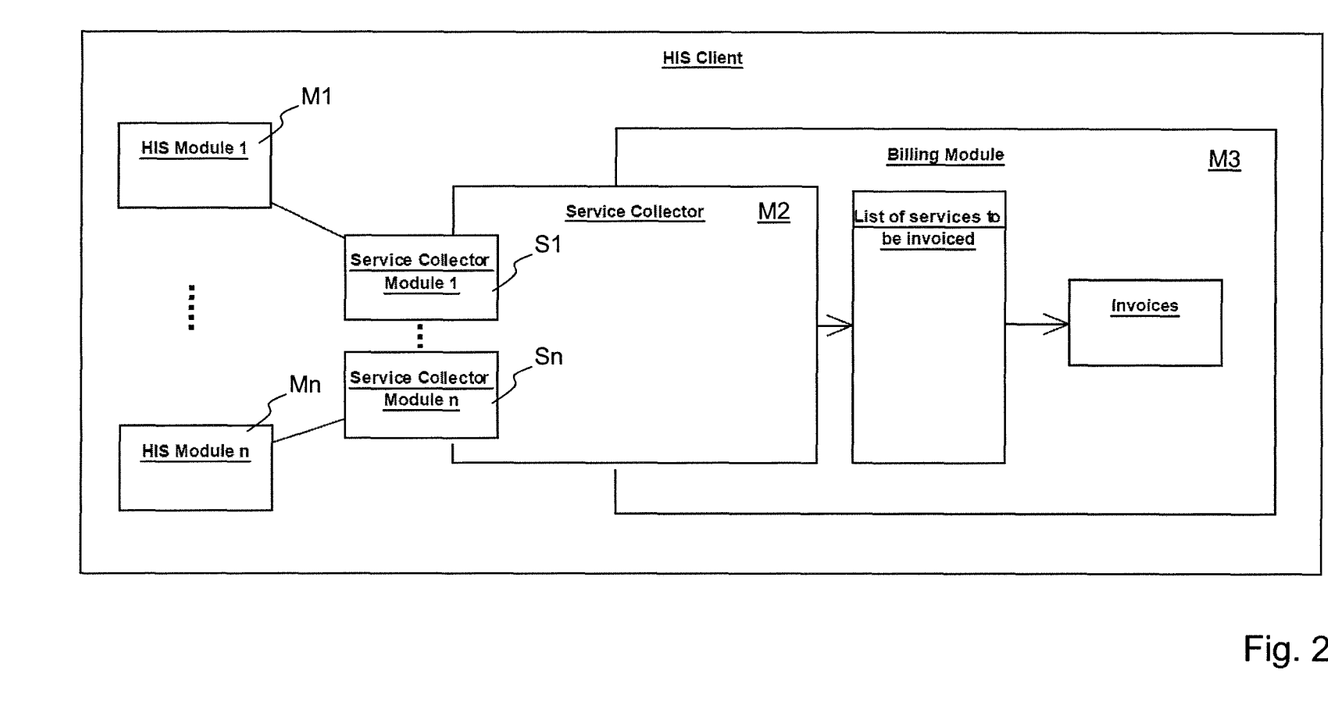
FIG. 2 shows an example of a second system for data processing.

FIG. 2 shows an example of a second system for data processing. The given example represents a particularly preferred application of the invention in a hospital information system (HIS). As will be described in more detail below, the second system corresponds to a HIS client by which a customizable and/or configurable assignment of chargeable services rendered to a patient or a medical case from all possible sources is achieved in order to provide a basis for an invoice relating to the rendered services.

According to the present example, a number of HIS modules M1 to Mn, which correspond to the first modules described above, are provided for generating services or for capturing data relating to services rendered to a patient or in connection with a medical case. In particular, the HIS modules M1 to Mn create services from internal service capturing, generated grouping results, organization structure configurations or external interfaces and assign them to the patient.

To each of the HIS modules M1 to Mn a service collector module S1 to Sn is assigned. The service collector M2, which corresponds to the second module described above, is configurable and/or customizable in such a way that for a given patient, a given medical case and/or a given accounting or billing mode one or more service collector modules S1 to Sn can be pre-defined, wherein the pre-defined service collector modules S1 to Sn call all of the corresponding assignment modules M1 to Mn for a chargeable patient or medical case, respectively. By this, a collection of services of configurable, i.e. pre-defined, assignment modules M1 to Mn can be extended anytime and can be simply achieved by configuring or pre-defining corresponding service collector modules S1 to Sn.

Service-related data, which correspond to the first data mentioned above, of the configured HIS modules M1 to Mn are collected by the service collector M2 and entered into a list of services to be invoiced. Upon completion of this list, according invoices are generated. As indicated in the example given in FIG. 2, the list of services to be invoiced and a sub-module for generating according invoices can be part of a billing module M3, which corresponds to the third module described above. Moreover, a part of the service collector M2 can also be integrated into the billing module M3. Alternatively, it is possible to provide the service collector M2 and the billing module M3 as separate modules which are connected via appropriate data links.

By the described application of the invention it is ensured that all service-related data captured and/or available at a pre-defined set of HIS modules M1 to Mn are forwarded to the billing module M3 such that all of these data are available in the billing module M3 at a desired point of time and, therefore, can be considered in a data processing step, in particular when calculating and/or generating invoices relating to the rendered services. Besides, the elucidations and advantages set forth above in connection with the example of FIG. 1 apply accordingly.

In the following, an example of a preferred data processing workflow is given by FIGS. 3 and 4.

Figure 3:
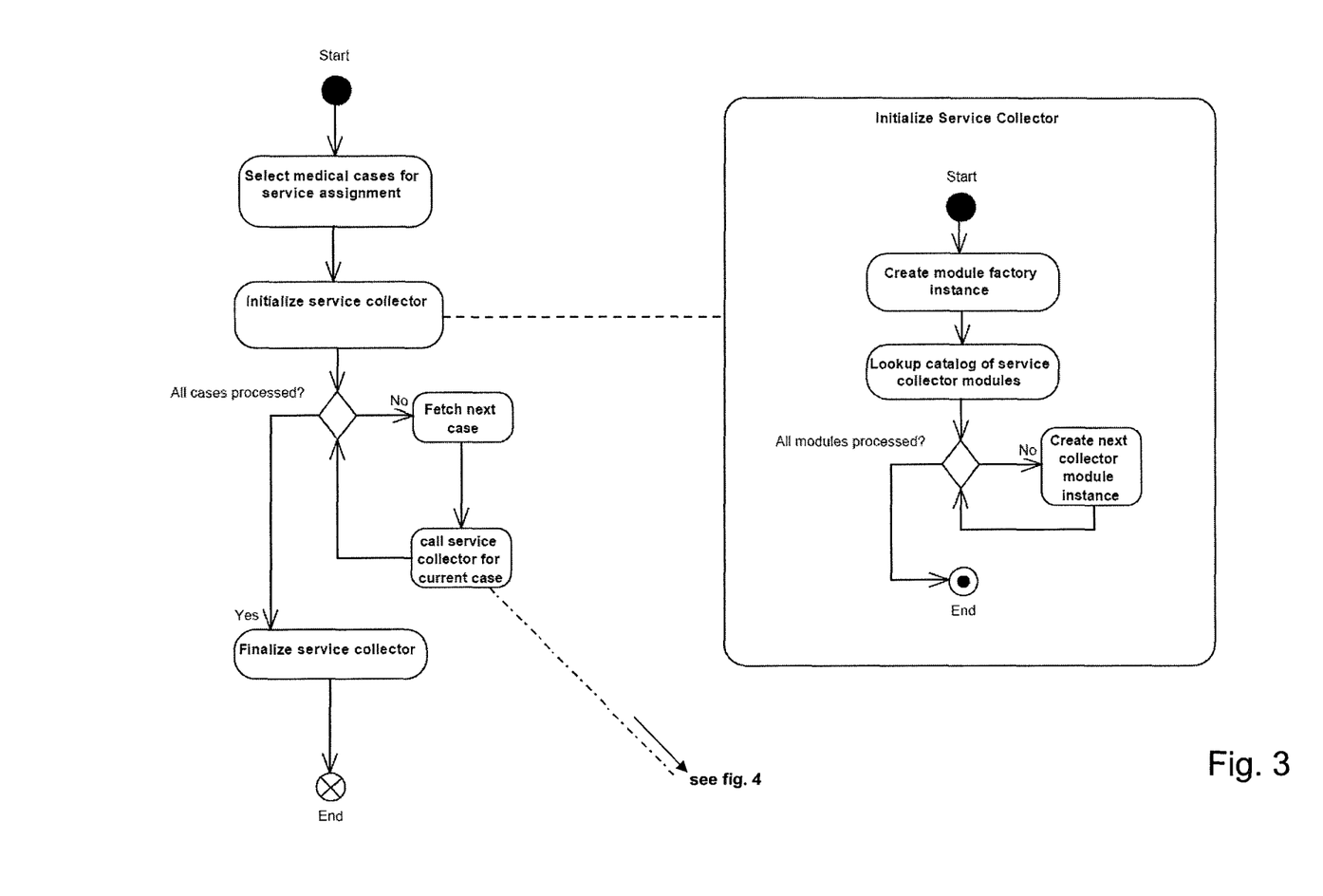
FIG. 3 shows an example of a first section of a data processing workflow.

As obvious from FIG. 3, after starting the data processing workflow medical cases, e.g. patients, for service assignment are selected, e.g. by a user. Then the service collector is initialized, wherein a module factory instance is created and a lookup catalogue of service collector modules is created, i.e. defined. In the case that not all of the service collector modules have been processed, a next service collector module instance is created. If all the service collector modules are processed, then the service collector initialization is terminated.

If not all of the selected medical cases have been processed, a next case is fetched and the service collector is called for the current medical case.

Figure 4:
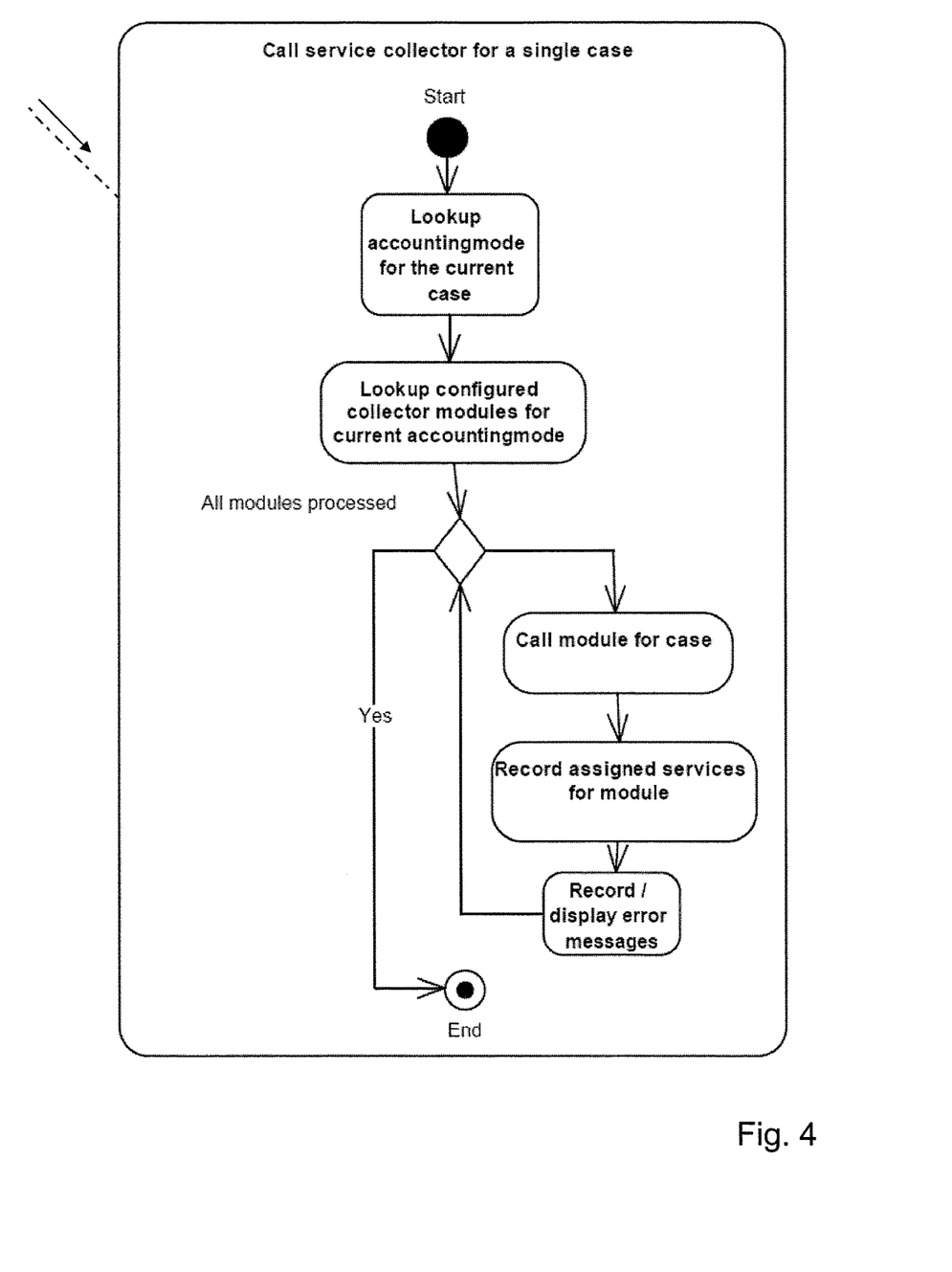
FIG. 4 shows an example of a second section of the data processing workflow.

As detailed in FIG. 4, upon starting the called service collector for a current case an accounting mode for the current case is determined, e.g. by a pre-defined list or lookup table. Then, the configured collector modules for the current accounting mode are determined, e.g. by a pre-defined list or lookup table.

If not all of the configured collector modules have been processed, a next module for the current medical case is called, the assigned services of this module are recorded or, if applicable, error messages are displayed. If all of the configured collector modules are processed, the call of the service collector for a single case is terminated.

As obvious from FIG. 3 again, it is examined whether all selected medical cases have been processed. If not, fetching the next case and calling the service collector for that case is repeated and so on. If yes, the service collector is finalized.

Figure 5:
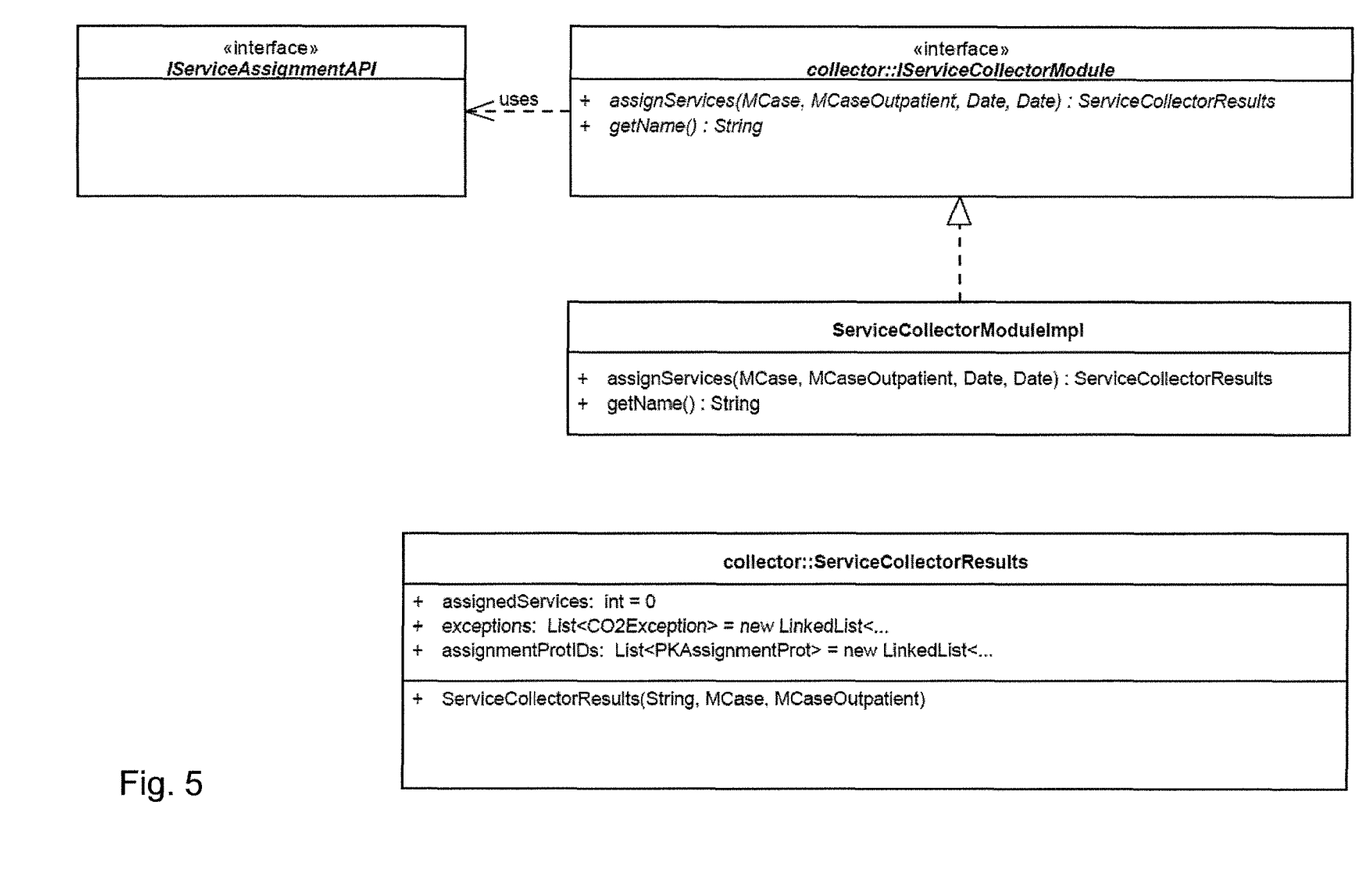
FIG. 5 shows examples of embodiments of components and/or modules of the system for data processing.
Figure 6:
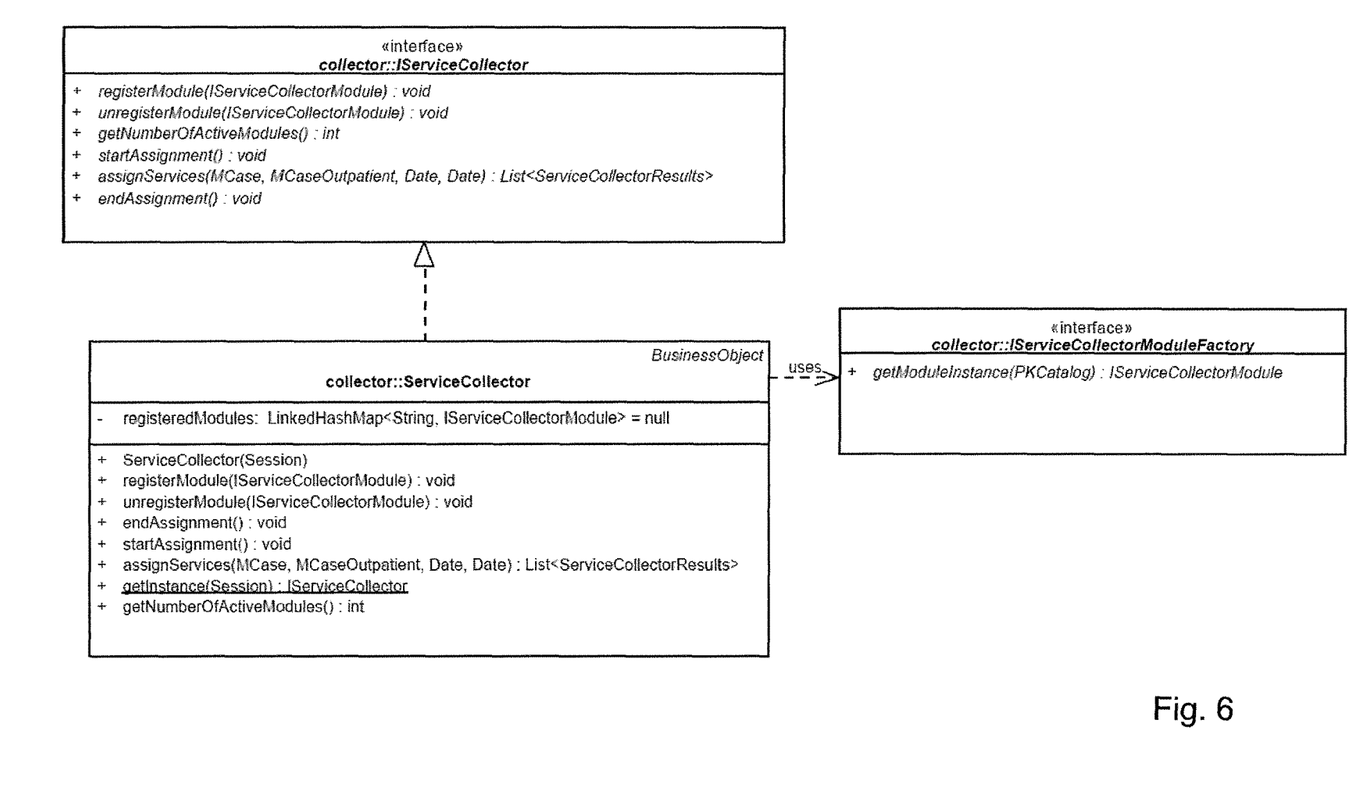
FIG. 6 shows examples of embodiments of further components and/or modules of the system for data processing.

FIGS. 5 and 6 show further preferred implementations of the system for data processing.

Service Collector Module

Preferably, the service collector module is implemented as a Java class, i.e. a class of data (attributes) and methods for processing these data in the class-based, object-oriented computer programming language Java. Java applications are typically compiled to bytecode (class file) that can run on any Java virtual machine (JVM) regardless of computer architecture.

The functions which have to be provided by this Java class in order to be used by the service collector framework are defined in an interface (collector::IService-Collector-Module) which contains a method for assigning services rendered to a medical case, i.e. an inpatient or outpatient furnished as a parameter, in a defined period of time.

For generating and furnishing the services to the accounting system a standardized import interface (IServiceAssignmentAPI) is used. By this it is ensured that the services are uniformly assigned to a medical case throughout all modules, i.e. assigned to a medical case independently from the respective type of the module. Moreover, while assigning a service one or more unique identification code(s) (ID) are generated. The framework provides functions for logging and, in the case of a later requirement of the module, determining the ID again.

In the case that a module is called several times for a medical case, it considers the status (assigned, billed, cancelled etc.) of already assigned services by the ID generated with the first assignment of services.

The decision as to the services which have to be assigned, depends on the logic of the modules.

The available service collector modules are communicated to the system via an extensible catalogue. A catalogue is a country-specific list of entries, the visibility and modifiability of which can be controlled by a user, i.e. the user can add his/her own service collector module implementation, if need arises. Alternatively, the catalogue is configured to be specifiable in a programming or implementation stage of the system only.

An entry into the catalogue for a service collector module comprises a unique ID, a name visible to the user, a period of validity, and a name of the implemented Java class.

In the following, examples for service collector modules are given for assigning:
- services within a certain period of time base on a stay of a patient in certain departments/stations/rooms
- case-based lump sums and procedural rates based on available grouping results (DRG, PEPP)
- services for the handling of co-payments (credit notes, reclaims, administration charges, reminder fees)
- external services (agreed with the payer) arising from an internal catalogue (tariff-neutral services)

Configuration of the Service Collector

Each medical case, i.e. inpatient or outpatient, in the system is labeled with a billing category which is, like the service collector modules, specified in a catalogue.

By 1: n links between the billing categories and the service collector modules it is controlled which service collector modules are called for each of the medical cases.

Service Collector

The service collector (collector::ServiceCollector) is responsible for the course of the assignment. It is realized as a singleton. The generation of the instance comprises a browsing of the catalogue of the service collector modules and a generation, via reflection by a factory defined by an interface (collector::IServiceCollectorModuleFactory), and registration of the available modules.

In the case that a medical case is furnished to the service collector, it determines the registered modules necessary for the given billing category by the service collector configuration and further delegates the call to the registered modules (ServiceCollectorModuleImpl).

The information contained in the return values (collector::ServiceCollector-Results, e.g. number of services rendered, possible error messages) are visualized for the user and the IDs of the assignments are logged, i.e. stored in a data base.

The invention claimed is:

1. A system for data processing comprising:
   at least two sensors that generate or capture first data;
   at least one first circuitry that retrieves the first data from sensors of the at least two sensors that correspond to at least one predefined set of sensors; and
   a second circuitry that processes the first data which were retrieved by the at least one first circuitry; wherein
   the at least one first circuitry selects the at least one predefined set of sensors from a plurality of predefined sets of sensors, and retrieves the first data from the sensors that correspond to the at least one predefined set of sensors; and
   the second circuitry processes the first data dependent upon a processing mode, and the at least one first circuitry selects the at least one predefined set of sensors from the plurality of predefined sets of sensors dependent upon the processing mode.

2. The system according to claim 1, wherein the at least one first circuitry forwards the first data to the second circuitry such that the first data are available in the second circuitry at a predefined point in time.

3. The system according to claim 1, wherein the processing mode depends upon a patient, to which the first data relate.

4. The system according to claim 1, wherein the at least one first circuitry assigns the processing mode to the at least one predefined set of sensors.

5. The system according to claim 1, wherein the at least one first circuitry generates one or more of the at least one predefined set of sensors.

6. The system according to claim 1, wherein the at least one first circuitry stores one or more of the at least one predefined set of sensors.

7. The system according to claim 1, wherein the second circuitry generates second data based on processing of the first data.

8. The system according to claim 7, wherein the second circuitry generates an output of the second data.

9. The system according to claim 1, wherein the at least two sensors generate and/or capture the first data upon one or more events related to a patient.

10. The system according to claim 9, wherein the one or more events related to the patient correspond to a treatment of and/or a service rendered to the patient.

11. The system according to claim 1, wherein the first data relates to a treatment of and/or a service rendered to a patient.

12. A method for data processing comprising:
   generating or capturing first data with at least two sensors;
   retrieving the first data with at least one first circuitry from sensors of the at least two sensors that correspond to at least one predefined set of sensors; and
   processing the first data which were retrieved by the at least one first circuitry with a second circuitry; wherein
   the at least one first circuitry selects the at least one predefined set of sensors from a plurality of predefined sets of sensors, and retrieves the first data from the sensors that correspond to the at least one predefined set of sensors; and
   the second circuitry processes the first data dependent upon a processing mode, and the at least one first circuitry selects the at least one predefined set of sensors from the plurality of predefined sets of sensors dependent upon the processing mode.

13. The system according to claim 8, wherein the second circuitry generates the output of the second data using a hardcopy device.

14. The system according to claim 1, wherein each of the at least two sensors is an optical sensor or an acoustic sensor.

* * * * *